(12) United States Patent
Liu et al.

(10) Patent No.: US 9,150,602 B2
(45) Date of Patent: Oct. 6, 2015

(54) PRECURSOR USED FOR LABELING HEPATORCYTE RECEPTOR AND CONTAINING TRISACCHARIDE AND DIAMIDE DEMERCAPTIDE LIGAND, METHOD FOR PREPARING THE SAME, RADIOTRACER AND PHARMACEUTICAL COMPOSITION OF THE SAME

(75) Inventors: Show-Wen Liu, Taoyuan County (TW); Yu Chang, Taoyuan County (TW); Cheng-Fang Hsu, Taoyuan County (TW); Ming-Che Tsai, Taoyuan County (TW); Tsung-Hsien Chiang, Taoyuan County (TW); Yueh-Feng Deng, Taoyuan County (TW); Kuei-Lin Lu, Taoyuan County (TW); Chih-Yuan Lin, Taoyuan County (TW); Da-Ming Wang, Taoyuan County (TW); Ching-Yun Li, Taoyuan County (TW)

(73) Assignee: Atomic Energy Council, Institute of Nuclear Energy Research, Taoyuan County (TW)

( * ) Notice: Subject to any disclaimer, the term of this patent is extended or adjusted under 35 U.S.C. 154(b) by 571 days.

(21) Appl. No.: 13/556,486

(22) Filed: Jul. 24, 2012

(65) Prior Publication Data
US 2014/0031533 A1    Jan. 30, 2014

(51) Int. Cl.
*C07H 15/18* (2006.01)
*C07H 1/00* (2006.01)

(52) U.S. Cl.
CPC . *C07H 15/18* (2013.01); *C07H 1/00* (2013.01)

(58) Field of Classification Search
CPC ....................................................... C07H 15/18
USPC ........................................................ 424/1.37
See application file for complete search history.

(56) References Cited

U.S. PATENT DOCUMENTS 8,551,447 B2 * 10/2013 Liu et al. ..................... 424/1.69

\* cited by examiner

*Primary Examiner* — Jake Vu
(74) *Attorney, Agent, or Firm* — Rosenberg, Klein & Lee

(57) ABSTRACT

A precursor used for labeling hepatocyte receptors and applied to radiotracers for imaging or pharmaceutical compositions for liver cancers is revealed. The precursor is a bifunctional compound. The bifunctional group includes a trisaccharide structure and a diamide dimercaptide ($N_2S_2$) ligand. The trisaccharide has high affinity to asialoglycoprotein receptors (ASGPR) on surfaces of hepatocytes while $N_2S_2$ ligand reacts with radioisotopes to form neutral complexes. Thus the precursor stays on surfaces of hepatocytes to provide radioisotope labeling or treatment effect of liver cancers.

19 Claims, 8 Drawing Sheets

PRECURSOR USED FOR LABELING HEPATORCYTE RECEPTOR AND CONTAINING TRISACCHARIDE AND DIAMIDE DEMERCAPTIDE LIGAND, METHOD FOR PREPARING THE SAME, RADIOTRACER AND PHARMACEUTICAL COMPOSITION OF THE SAME

BACKGROUND OF THE INVENTION

1. Fields of the invention

The present invention relates to a precursor used for labeling hepatocyte receptors, a method for preparing the same, a radiotracers for imaging, and a pharmaceutical composition of the same, especially to a bifuncitonal precursor containing trisaccharide and a diamide dimercaptide ($N_2S_2$) ligand, a method for preparing the same, a radiotracer, and a pharmaceutical composition of the same.

2. Descriptions of Related Art

Faced with an increasingly ageing and more competitive society, various kinds of diseases such as cancers, cerebrovascular diseases, diseases of nervous system and heart diseases seriously threaten our health. For early diagnosis, early treatment and prevention of these diseases, the development of functional and molecular techniques of diagnostic and treatment of the above diseases have become matters of great urgency.

In medical techniques available now, isotope tracer techniques and serum biochemical markers are commonly used for detecting human diseases or functional disorders. Both have advantages of safety, non-invasion, convenience and accuracy. As to the treatment target, the most popular applications are related to follow-up and treatment of liver diseases. Among liver diseases, liver fibrosis represents the liver's response to some simulates such as necrosis and inflammation and these stimulates arouse durative hyperplasia of fibril connective tissue in the liver. Liver fibrosis is reversible in early stage. The advanced liver fibrosis results in cirrhosis and cirrhosis is generally irreversible.

The main method for testing and diagnosis of liver fibrosis is liver puncture to get liver biopsy. The method has following shortcomings. Firstly, this is an invasive test method. Secondly, the method has the risk of complications including pain, bleeding, peritonitis, etc. The third, if the liver tissue obtained is too small or too short, there is an error in test results and clinical diagnosis. The fourth is that the test is with low reproducibility. The test is unable to be applied to patients on clinical repetitively for monitoring patient's conditions dynamically According to international standard, liver fibrosis includes four stages. In the F1/F2(mild/moderate) stages, liver fibrosis is reversible and the treatment effect is optimal. The liver tissue can be back to normal state. In the F 3 stage (advanced fibrosis), the treatment effect is poor and liver fibrosis is severe. As to the stage F4, liver fibrosis is worsen to liver cirrhosis and is irreversible. Thus the earlier liver fibrosis is detected, the better the treatment effect of the patient.

Human cells have specific receptors on surfaces to accept some specific proteins or peptides. According to this specificity, some proteins or peptides are labeled with radioactive nuclides and are delivered into human bodies. Then the labeled proteins or peptides achieve higher concentration in specific organs or tissues so as to diagnose or treat diseases by using nuclear imaging.

In the past, bifunctional group ligand is used together with technetium compounds or rhenium compounds to label proteins or peptides. For example, compound S-Hynic with bifunctional group includes an active carboxylic acid that is used to form a strong amide bond with proteins or peptides. Moreover, it contains a pyridyl group and hydrazo structure that bond to $^{99m}Tc$. While being used together with auxiliary chelating agents such as Tricine, S-Hynic reacts with technetium or rhenium to get stable complexes. However, S-Hynic solution is photosensitive and is not convenient in use. Thus there is a need to find out more stable organic compounds with bifunctional groups.

There are about two hundred thousand asialoglycoprotein receptors (ASGPR) on surfaces of mammalian heptocytes. The asialoglycoprotein receptor (ASGPR) is a liver-specific transmembrane glycoprotein that mediates endocytosis, removes desialylated glycoproteins, and involves in lipoprotein catabolism. The ASGPR also has high affinity to galactose (Gal) and N-acetylgalactosamine (GalNAc). Especially when a ground substance contains tri-Gals or N-acetylgalactosamine, it has higher affinity to ASGPR on surfaces of hepatocytes, almost $10^6$ times than a substrate with a single N-acetylgalactosamine. Based on this characteristic, YEE (ah-GalNAc)$_3$ has been used as a drug/gene carrier for drug or gene delivery to hepatocytes.

It is learned that carboxylic acids can bind to alcohols, saccharides(carbohydrates), amines, amino acids, peptides and proteins while diamide dimercaptide ($N_2S_2$) ligands bind to radioisotopes such as technetium or rhenium. But now there is no radioactive tracer for imaging of hepatocyte receptors formed by Gal, GalNAc and $N_2S_2$ ligand.

Both Gal and GalNAc have specificity to hepatic lectin. Once radioisotopes are connected to Gal and GalNAc of glycoprotein, nuclear pharmaceuticals are optimally delivered to the targeted liver cells and entered the cells by endocytosis for functional imaging or therapeutic use. The design of glycosyl group is not revealed yet in the field of nuclear medicine. Thus a preparation method for hepatocyte receptor labeled precursor containing trisaccharide and a diamide dimercaptide ($N_2S_2$) ligand is provided so as to increase sensitivity and specificity of nuclear medicine tests.

SUMMARY OF THE INVENTION

Therefore it is a primary object of the present invention to provide a precursor used for labeling hepatocyte receptors and containing trisaccharide and a diamide dimercaptide ($N_2S_2$) ligand, a method for preparing the same, a radiotracer, and a pharmaceutical composition of the same. The $N_2S_2$ ligand is used to chelate radioisotopes and the three active carboxylate ester that reacts with compounds containing amino groups to form amide bonds. Thus a bifunctional compound is obtained. The bifunctional compound can bond to polyols, saccharides, amines, amino acids, peptides or proteins so as to stay on surfaces of hepatocytes. On the other hand, the compound can also bond to other compounds such as $TcO^{3+}$, $ReO^{3+}$, etc. and then is applied to research and production of nuclear pharmaceuticals.

It is another object of the present invention to provide a precursor used for labeling hepatocyte receptors and containing trisaccharide and a diamide dimercaptide ($N_2S_2$) ligand, a method for preparing the same, a radiotracer, and a pharmaceutical composition of the same in which trityl groups are used to protect thiol groups of $N_2S_2$ ligand. During the complex reaction, the protecting groups are released automatically and there is no need to remove the protecting groups in advance before the complex reaction. Thus this is more convenient to use.

It is a further object of the present invention to provide a precursor used for labeling hepatocyte receptors and containing trisaccharide and a diamide dimercaptide ($N_2S_2$) ligand, a method for preparing the same, a radiotracer, and a pharmaceutical composition of the same in which galactoside ah-GalNAc$_4$ is used as a functional group and the galactoside has high affinity to asialoglycoprotein receptors (ASGPR) on surfaces of heptocytes so as to ensure imaging effect of liver and treatment effect of liver cancers.

It is a further object of the present invention to provide a precursor used for labeling hepatocyte receptors and containing trisaccharide and a diamide dimercaptide ($N_2S_2$) ligand, a method for preparing the same, a radiotracer, and a pharmaceutical composition of the same. During the synthesis of galactoside ah-GalNAc$_4$, benzyloxycarbonyl (carboxybenzyl, cbz) is an amine protecting group used to protect an amino group of 6-aminohexanol. Thus trifluoroacetyl compounds are no more used. This protecting group is easily to be released during hydrogenation. Moreover, other functional groups of the molecule are not affected by this protecting group during hydrogenation.

In order to achieve the above objects, a precursor used for labeling hepatocyte receptors and containing trisaccharide and a diamide dimercaptide ($N_2S_2$) ligand, a method for preparing the same, a radiotracer, and a pharmaceutical compositions of the same are provided. The method for preparing the precursor includes a plurality of steps. Firstly synthesize a carboxylic acid of a bifunctional chelating agent containing a diamide dimercaptide ($N_2S_2$) ligand. Then the carboxylic acid is amidated to form an amide of the bifunctional chelating agent containing $N_2S_2$ ligand and hydrolyze the amide to get three polycarboxyl groups. Next synthesize three galactosides. At last, use the galactosides to amidate the polycarboxyl groups of the amide and get a precursor used for labeling hepatocyte receptors and containing trisaccharide and a $N_2S_2$ ligand. Moreover, the precursor can be used to prepare radiotracers for imaging and form a pharmaceutical composition for treating liver cancers.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Conventional labeling of human liver cells has shortcomings of poor labeling effect, low stability and inconvenience in use. The present invention provides a compound with a specific chemical structure and a method for preparing the same that overcome the above problems.

Figure 1:
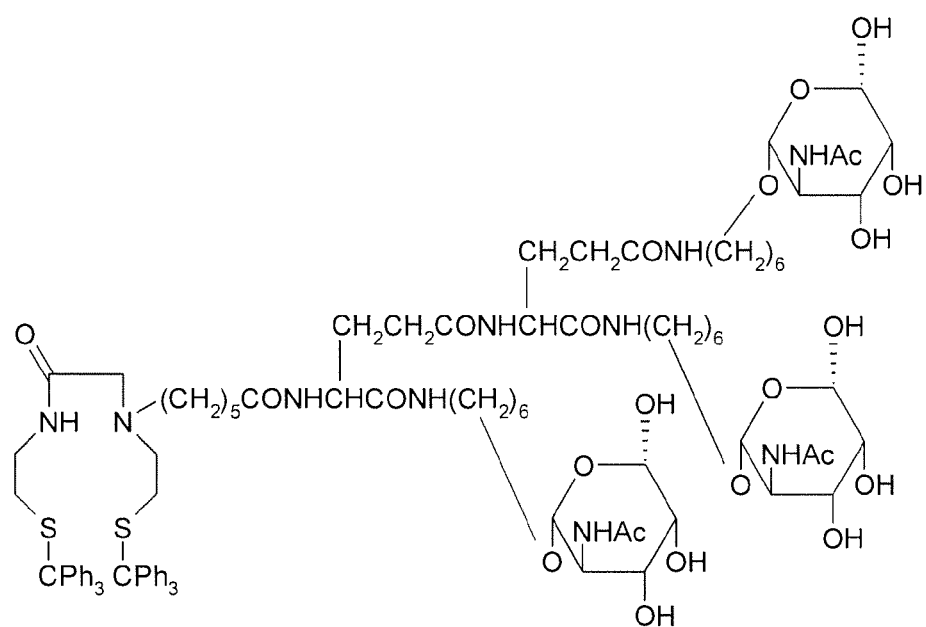
FIG. 1 shows a chemical structure of a precursor used for labeling hepatocyte receptors and containing trisaccharide and a diamide dimercaptide ($N_2S_2$) ligand according to the present invention.

Refer to FIG. 1, it is a schematic drawing showing a chemical structure of a precursor used for labeling hepatocyte receptors and containing tri-galactose and a diamide dimercaptide ($N_2S_2$) ligand of the present invention. Without chelating radioisotopes, the $N_2S$, ligand is protected by a trityl group because thiols are easy to be oxidized. Before a complex reaction occurs between the $N_2S_2$ ligand and radioisotopes to produce neutral complexes, a protecting group for thiol groups needs to be removed. The trityl group used in the present invention is released during the complex reaction and there is no need to remove the trityl group in advance. Thus the trityl group is convenient in use.

Beside the $N_2S_2$ ligand, the present invention further includes trisaccharide that has high affinity and specificity to ASGPR and enters human HepG2 selectively by endocytosis. In other words, this trisaccharide structure helps the precursor of the present invention to be targeted to liver tumor cells. Then the precursor is delivered into liver tumor cells by endocytosis so as to achieve radioactive labeling or therapeutic use.

Figure 2:
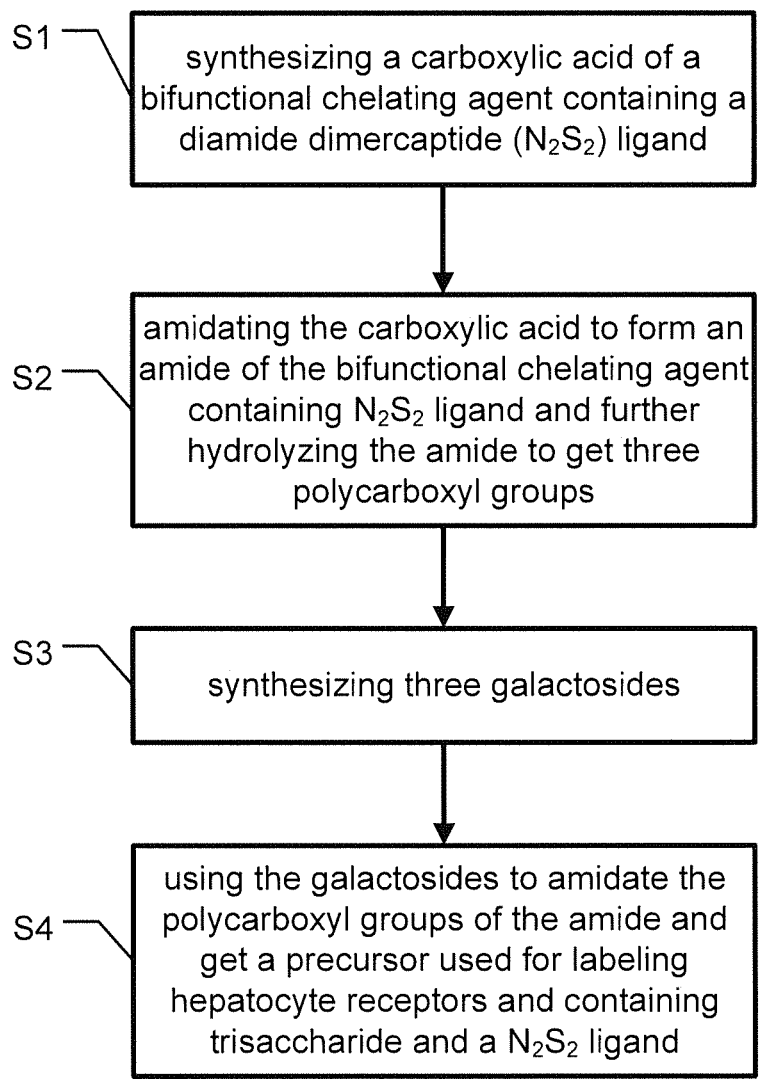
FIG. 2 is a flow chart showing steps of preparing precursor used for labeling hepatocyte receptors and containing trisaccharide and a diamide dimercaptide ($N_2S_2$) ligand according to the present invention.

Refer to FIG. 2, a flow chart of a method for preparing the precursor used for labeling hepatocyte receptors and containing tri-galactose and $N_2S$, ligand is revealed. The method includes following steps.

Step S1: Synthesize a carboxylic acid of a bifunctional chelating agent containing a diamide dimercaptide ($N_2S_2$) ligand;

Step S2: Amidate the carboxylic acid to form an amide of the bifunctional chelating agent containing the diamide dimercaptide ($N_2S_2$) ligand; further hydrolysis the amide to form three polycarboxyl groups;

Step S3: Synthesize three galactosides;

Step S4: Use the galactosides to amidate the polycarboxyl groups of the amide and get a precursor used for labeling hepatocyte receptors and containing trisaccharide and a $N_2S_2$ ligand.

In these steps, the key technique features on the construction of the diamide dimercaptide ($N_2S_2$) ligand and trisaccharide structure. That means to synthesize a bifunctional compound that chelates radioactive isotopes and has high affinity to ASGPR.

Figure 3:
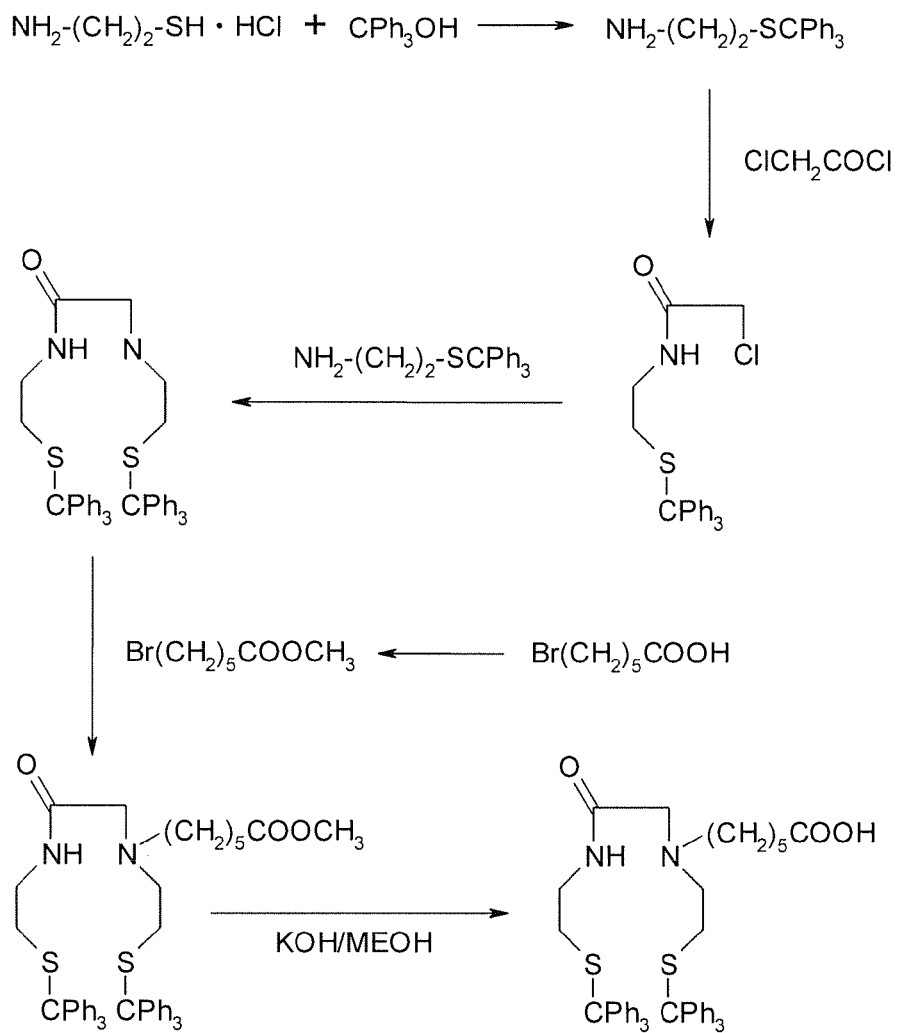
FIG. 3 shows a part of flow chart of synthesis of an embodiment according to the present invention.

In the step S1, the carboxylic acid of a bifunctional chelating agent containing a diamide dimercaptide ($N_2S_2$) ligand used is 7,10-diaza-9-oxo-7-[2-((triphenylmethyl)thio)-ethyl]-12-[(triphenylmethyl)thio]dodecanoic acid. The detailed steps for synthesis of this carboxylic acid are shown in the FIG. 3.

Step (1): For protecting thiol groups, take 2-thioethylamine hydrochloride and triphenylmethanol as reactants and boron trifluoride-diethyl ether complex is used as a catalyst to get 2-[(triphenylmethyl)thio]ethylamine. The reaction temperature is 72 degrees Celsius and the reaction time is 4 hours.

Step (2): Use 2-[(Triphenylmethyl)thio]ethylamine and chloroacetyl chloride to carry out the amidation reaction in trichloromethane solution so as to produce N-[2-((Triphenylmethyl)thio)ethyl]-chloroacetamide.

Step (3): Take 2-[(Triphenylmethyl)thio]ethylamine, N-[2-((Triphenylmethyl)thio)ethyl]-chloroacetamide and use triethylamine used as a reagent to carry out the substitution reaction in dichloromethane solution. Thus an amine-amide-thiol ligand is produced. The reaction temperature of the substitution reaction is 55° C. and the reaction time is 48 hours.

Step (4): Dissolve 6-bromohexanoic acid and thionyl chloride in absolute methanol solution to carry out the esterification reaction and get methyl 6-bromohexanoate. The reaction temperature of the esterification reaction is 25° C. and the reaction time is 24 hours.

Step (5): Take the amine-amide-thiol ligand and methyl 6-bromohexanoate and use sodium hydroxide (NaOH) as a reagent to carry out the substitution reaction in acetonitrile solution and get methyl 7,10-diaza-9-oxo-7-[2-((triphenylmethyl)thio)-ethyl]-12-[(triphenylmethyl)thio]dodecanoate. The reaction temperature of the substitution reaction is 85° C. and the reaction time is 24 hours.

Step (6): Hydrolyze methyl 7,10-diaza-9-oxo-7-[2-((triphenylmethyl)thio)-ethyl]-12-[(triphenylmethyl)thio]dodecanoate in alkaline methanol solution to get 7,10-diaza-9-oxo-7-[2-((triphenylmethyl)thio)-ethyl]-12-[(triphenylmethyl)thio]dodecanoic acid.

Figure 4:
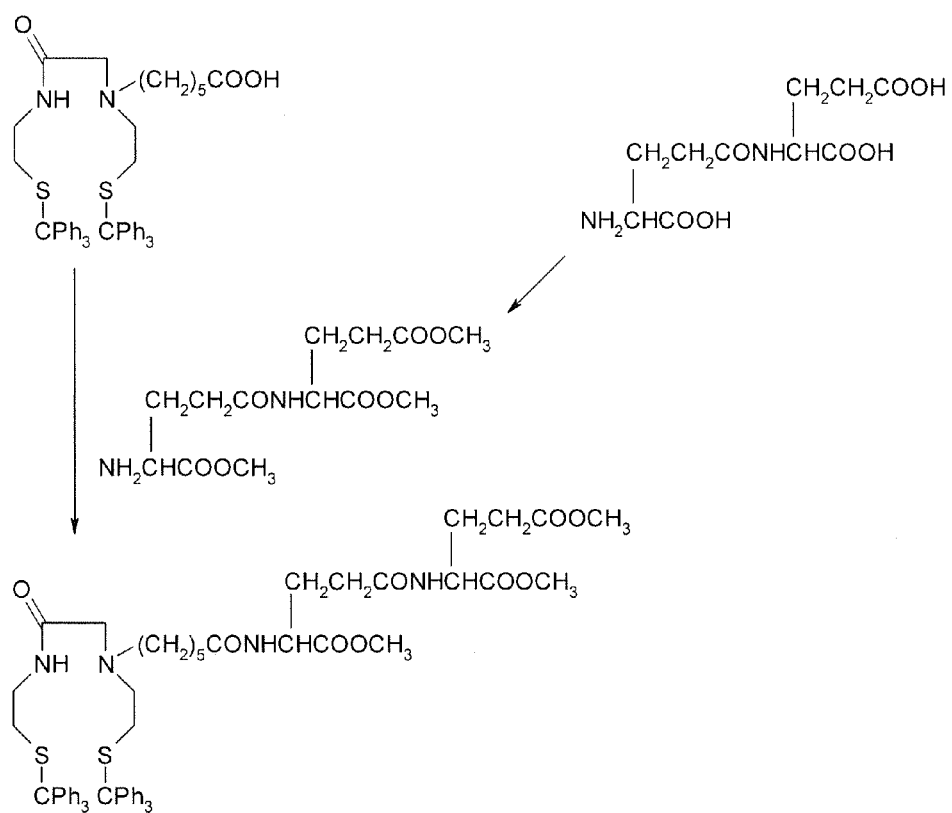
FIG. 4 shows a part of flow chart of synthesis of an embodiment according to the present invention.

After getting this carboxylic acid, take the step S2 to form amide by amidation of the carboxylic acid and get trimethyl-γ-L-glutamyl-L-glutamyl-7,10-diaza-9-oxo-7-[2-(triphenylmethyl)thioethyl]-12-[(triphenylmethyl)-thio]dodecanamide. The detailed steps are shown in the FIG. 4. The steps are as followings.

Step (7) Dissolve γ-L-glutamyl-L-glutamic acid and thionyl chloride in absolute methanol solution to carry out the esterification reaction and get methyl γ-L-glutamyl-L-glutamate; and Step (8) Take methyl γ-L-glutamyl-L-glutamate and the carboxylic acid and use 1,3-dicyclohexylcarbodiimide as well as N-hydroxysuccinimide as a reagent to carry out the amidation reaction in chloroform solution and get trimethyl-γ-L-glutamyl-L-glutamyl-7,10-diaza-9-oxo-7-[2-(triphenylmethyl)thioethyl]-12-[(triphenylmethyl)-thio]dodecanamide.

Figure 5:
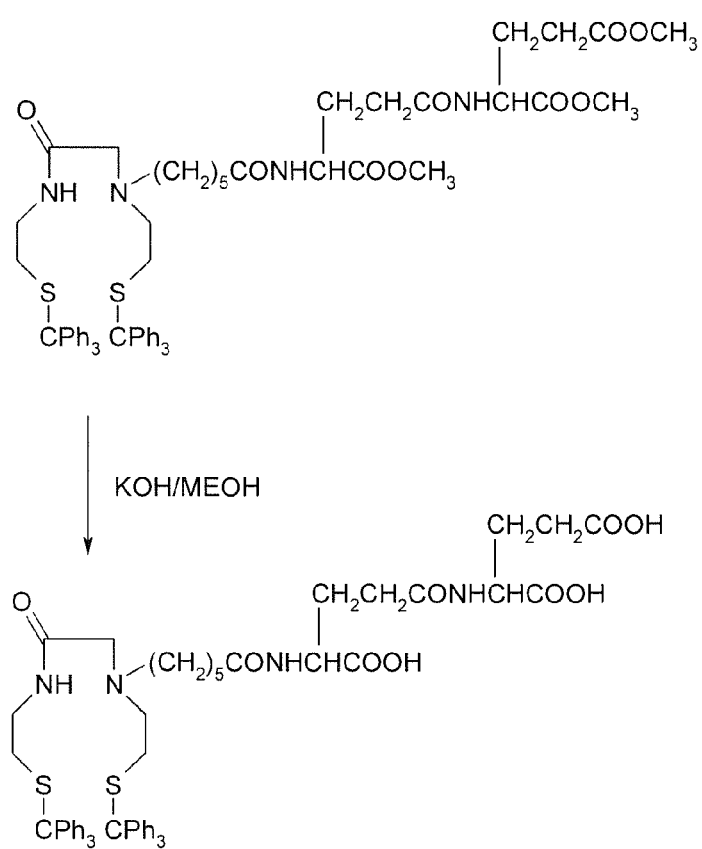
FIG. 5 shows a part of flow chart of synthesis of an embodiment according to the present invention.

Refer to FIG. 5, trimethyl-γ-L-glutamyl-L-glutamyl-7,10-diaza-9-oxo-7-[2-(triphenylmethyl)thioethyl]-12-[(triphenylmethyl)-thio]dodecanamide is hydrolyzed to get compound DODGA with three polycarboxylic groups. The polycarboxylic groups in the present invention are used to bond the galactosides.

Figure 6:
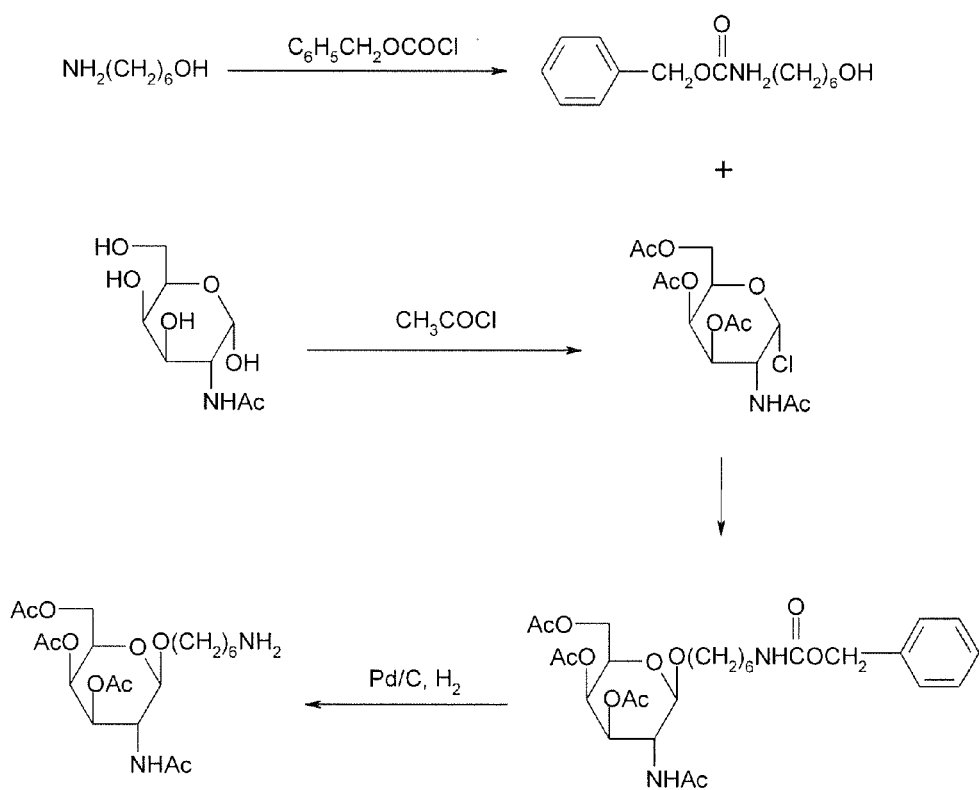
FIG. 6 shows a part of flow chart of synthesis of an embodiment according to the present invention.

After completing the step S2, run the step S3 to synthesize compound ah-GalNAc$_4$ containing three galactosides. The galatoside is 6'-aminohexyl-2-acetamido-3,4,6-tri-O-acetyl-2-deoxy-β-D-galactoside (ah-GalNAc$_4$). Refer to FIG. 6, it shows detailed steps for preparing the above galatoside.

Step (9): Use 6'-aminohexanol and benzyl chlorocarbonate to carry out an amino protecting reaction and get a 6'-(N-Benzyloxycarbonyl)aminohexanol.

Step (10): Take N-acetyl-D-galactosamine and acetyl chloride to react at 10° C. and get 2-Acetamido-2,4,6,-tri-O-acetyl-1-chloro-1,2-dideoxy-α-D-galactopyranose.

Step (11): Use 6'-(N-Benzyloxycarbonyl)aminohexanol and 2-Acetamido-2,4,6,-tri-O-acetyl-1-chloro-1,2-dideoxy-α-D-Galactopyranose to perform substitution reaction in a mixture solution of toluene and nitromethane with a catalyst of mercuric cyanide and get 6'-(N-Benzyloxycarbonyl)amino-hexyl-2-acetamido-3,4,6-tri-O-acetyl-2-deoxy-β-D-galactopyranoside.

Step (12) Hydrogenize/reduce 6'-(N-Benzyloxycarbonyl)aminohexyl-2-acetamido-3,4,6-tri-O-acetyl-2-deoxy-β-D-galactopyranoside in alcohol and in the presence of a palladium carbon catalyst to get the 6'-aminohexyl-2-acetamido-3,4,6-tri-O-acetyl-2-deoxy-β-D-galactoside.

During the synthesis process of the above galactoside, a plurality of protecting groups can be used. Which protecting group is optimal depends on the use of the compound. For convenience of the following procedures, carboxybenzyl is used as the protecting group. Carboxybenzyl is easy to be released and other functional groups of the molecule are not affected by carboxybenzyl during hydrogenation process.

6'-(N-Benzyloxycarbonyl)aminohexyl-2-acetamido-3,4,6-tri-O-acetyl-2-deoxy-β-D-galactopyranoside obtained in the step S11 is separated and purified by liquid chromatography. Generally, a Sephadex LH-20 column is used for liquid chromatography. However, the Sephadex LH-20 column is quite expensive. The present invention uses silica gel to replace Sephadex LH-20 media. The purification effect is good and the cost is significantly reduced.

The galactoside ah-GalNAc$_4$ obtained by hydrogenation/reduction in the step S12 doesn't need to be separated and purified. If a semi-product of the galactoside ah-GalNAc$_4$ before hydrogenation is with high purity, only toluene is produced during the hydrogenation process. The toluene is extremely volatile so that it will evaporate completely without residues during concentration processes. If a semi-product of the galactoside ah-GalNAc$_4$ before hydrogenation is not of sufficient purity, the product obtained after hydrogenation needs to be separated and purified. The process is similar to that of the step S11, a silica gel column for liquid chromatography is used for separation and purification.

Figure 7:
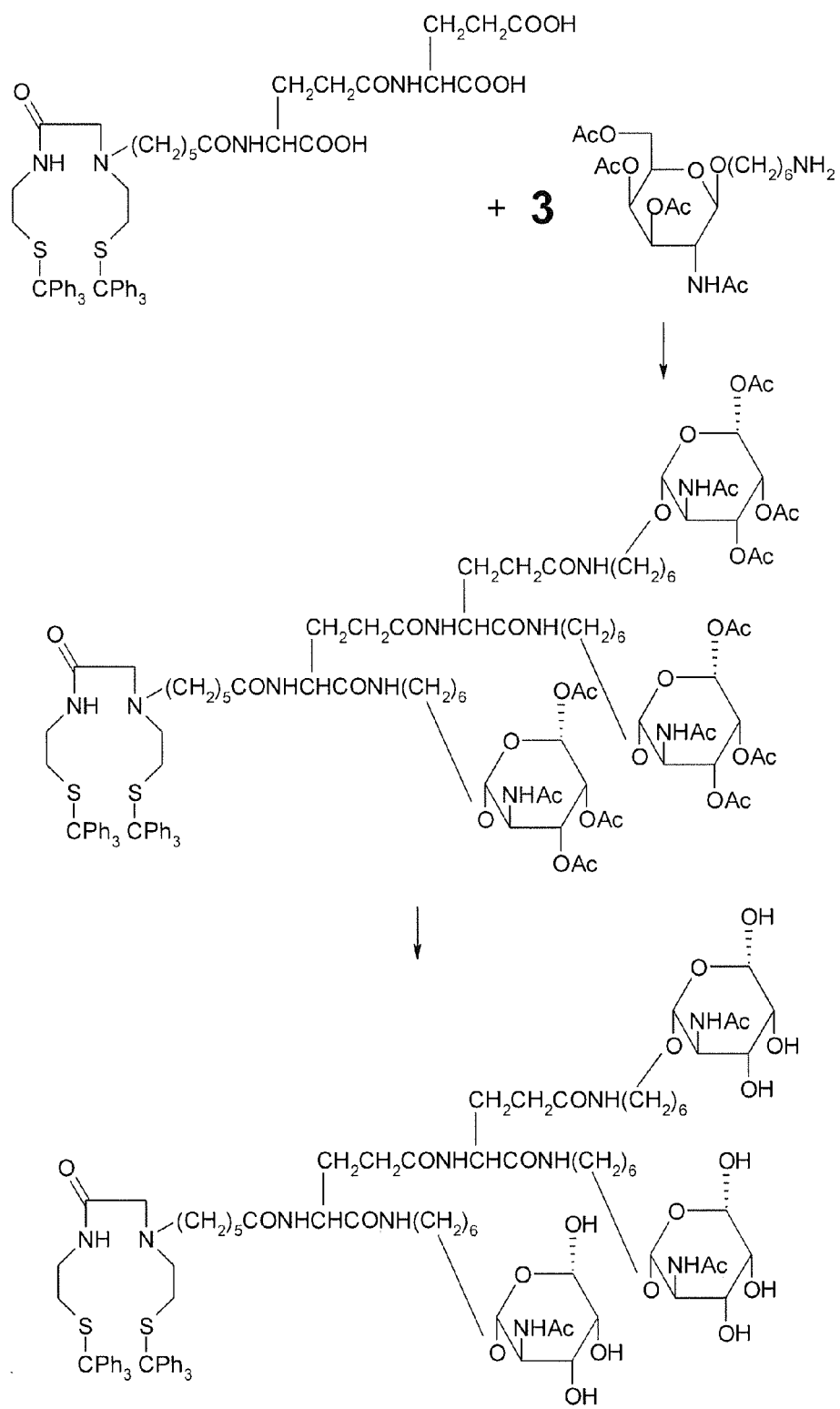
FIG. 7 shows a part of flow chart of synthesis of an embodiment according to the present invention.

The galactoside ah-GalNAc$_4$ obtained is used to connect with the compound DODGA with three polycarboxylic groups previously prepared so as to form (ah-GalNAc)$_3$-DODGA that is a precursor used for labeling hepatocyte receptors and containing trisaccharide and a diamide dimercaptide (N$_2$S$_2$) ligand according to the present invention. Refer to FIG. 7, the steps are as followings.

Step (13): Activate the carboxylic acid of DODGA to react with ah-GalNAc$_4$ and use 1,3-dicyclohexylcarbodiimide as well as N-hydroxysuccinimide as a reagent to carry out the amidation reaction in chloroform solution and get 6-Tri-o-(2'-acetamido-3',4',6'-tri-o-acetyl-2'-deoxy-β-D-galactopyranoside) hexyl 7,10-diaza-9-oxo-7-[2-(triphenylmethyl)thioethyl]-12-[(triphenylmethyl)thio]-dodecanamido-γ-L-glutamyl-L-glutamate; and Step (14): Hydrolyze 6-Tri-o-(2'-acetamido-3',4',6'-tri-o-acetyl-2'-deoxy-β-D-galactopyranoside) hexyl 7,10-diaza-9-oxo-7-[2-(triphenylmethyl)thioethyl]-12-[(triphenylmethyl)thio]-dodecanamido-γ-L-glutamyl-L-glutamate with sodium methylate to get 6-Tri-o-(2'-acetamido-3',4',6'-trihydroxy-2'-deoxy-β-D-galactopyranoside) hexyl 7,10-diaza-9-oxo-7-[2-(triphenylmethyl)thioethyl]-12-[(triphenylmethyl)thio]-dodecanamido-γ-L-glutamyl-L-glutamate, (ah-GalNAc)$_3$-DODGA.

While in use, radioactive isotope compound MO$^{3+}$ is bound to diamide dimercaptide (N$_2$S$_2$) ligand to form a neutral complex. Now a trityl group for protecting thiol group in the N$_2$S$_2$ ligand is removed by dissolving (ah-GalNAc)$_3$-DODGA in trifluoroacetic acid and adding excess amount of triethylsilane into the solution. Thus the trityl group is released from thiol to form solid insoluble in trifluoroacetic acid. Users can remove the solid by filtering or wash the solid with n-Hexane. This is convenient and simple.

Figure 8:
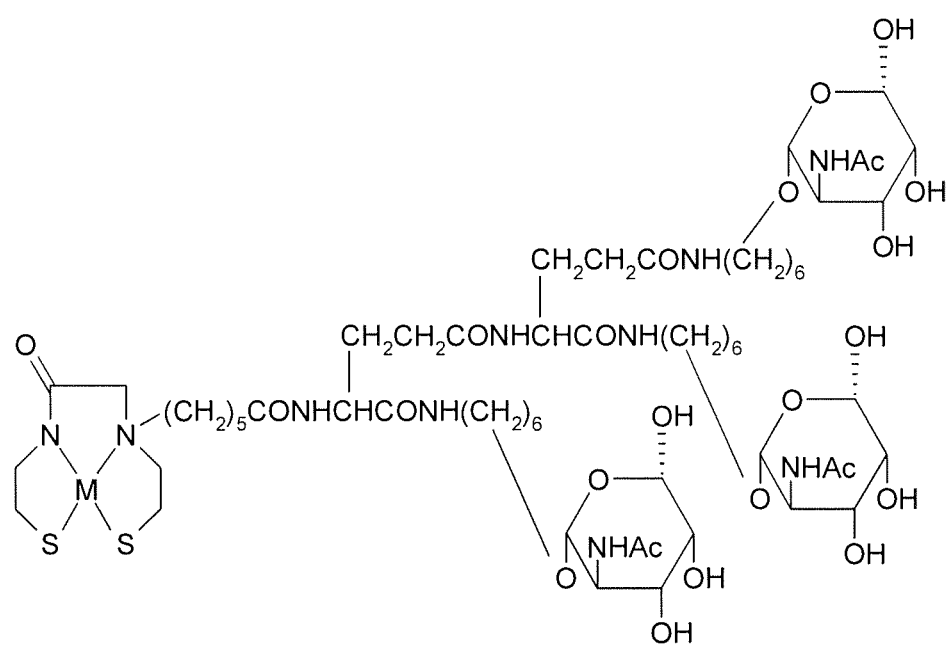
FIG. 8 shows a chemical structure a radiotracer or a pharmaceutical composition according to the present invention.

Besides the precursor used for labeling hepatocyte receptor and containing trisaccharide and a diamide dimercaptide (N$_2$S$_2$) ligand and the method for preparing the same, the present invention also reveals a radiotracer or a pharmaceutical composition of the same for treatment of liver cancers. Refer to FIG. 8, a graph showing chemical structure of radiotracers for imaging or pharmaceutical composition of the precursor used for labeling hepatocyte receptors and containing trisaccharide and diamide dimercaptide (N$_2$S$_2$) ligand is disclosed. M is a radioactive isotope such as $^{99m}$Tc, $^{188}$Re of $^{111}$In that is used to label liver cancer cells or treat liver cancer.

Beside $N_2S_2$ ligand used to chelate radioisotopes, the present invention also includes a trisaccharide structure. The trisaccharide structure has high affinity and specificity to ASGPR. Moreover, the trisaccharide structure is selectively taken into human liver cancer cell line HepG2 by endocytosis. Thus this structure helps the present invention to be targeted to liver cancer cells and enable the radioisotope to inhibit or kill the liver tumors. Therefore the pharmaceutical composition can be applied to treat liver cancers. Furthermore, due to excellent performance on the targeting, the precursor can be used as materials for radiotracers, used to label or treat liver cancer cells.

The compound of the present invention-(ah-GalNAc)$_3$-DODGA contains galactoside-ah-GalNAc$_4$ and has high affinity to ASGPR on surfaces of hepatocytes. Before use, there are some protecting groups for protecting thiol groups so that the compound is with high stability. Moreover, there is no need to remove the protecting groups in advance before reacting with radioisotope to form complexes. Thus a radiotracer for detecting liver fibrosis or a pharmaceutical composition for treatment of liver cancers associated with the precursor of the present invention is high-efficient and of significant medical values.

The followings are details and related parameters of each step according to the present invention.

Synthesis of 2-[(Triphenylmethyl)thio]ethylamine

Dissolve 2-thioethylamine hydrochloride (5 g, 44.2 mmol), triphenylmethanol (11 g, 42.5 mmol) and triethylamine (7 mL, 49.9 mmol) in 100 mL chloroform. Heat and reflux until the solution temperature reaches a certain temperature, slowly drop a catalyst borontrifluoride ethyl ether complex (15 mL, 119.5 mmol) into the solution and continue heating and reflux for 4 hours. Then cool down, add sodium bicarbonate aqueous solution into the solution and stir the mixture. White solid product is precipitated out immediately. Get the solid by suction filtration, wash the solid with water, and dry the solid. Thus solid product 2-[(triphenylmethyl)thio]ethylamine (14.0 g, 99%) is obtained.

Compound Data of the Product:

IR (neat) v 3381 ($NH_2$) cm$^{-1}$.

$^1$H NMR (CDCl$_3$) δ 7.42 (m, 3H, Ph), 7.30 (m, 12H, Ph), 2.58 (t, J=6.6 Hz, 2H, $CH_2$N), 2.32 (t, J=6.6 Hz, 2H, $CH_2$S), 1.45 (br, 2H, $NH_2$).

$^{13}$C NMR (CDCl$_3$) δ 144.80, 192.52, 127.81 and 126.60 (Ph), 66.51 (CPh), 40.94 ($CH_2$N), 36.09 ($CH_2$S).

MS m/z 319 (M$^+$), 243((CPh$_3$)$^+$).

Synthesis of
N-[2-((Triphenylmethyl)thio)ethyl]-chloroacetamide

Dissolve 2-[(triphenylmethyl)thio]ethylamine (5.24 g, 16.4 mmol) and triethylamine (2.76 mL, 19.6 mmol) in 150 mL dichloromethane. Chloroacetyl chloride (1.56 mL, 19.6 mmol) is dissolved in 20 mL chloroform. Being cooled down with an ice bath, slowly drop chloroacetyl chloride into the solution. Then stir the solution at room temperature for 2 hours. Next wash organic phase with followings in turn: 2N hydrochloric acid solution (120 mL), and saturated sodium bicarbonate aqueous solution (100 mL). The organic phase is dehydrated by anhydrous sodium sulfate (Na$_2$SO$_4$) and then is concentrated in vacuo to yield yellow oily N-[2-((Triphenylmethyl)thio) ethyl]-chloroacetamide (5.62 g, 86.6%).

Compound Data of the Product:

IR (neat) v 3413 and 3306 (NH), 1662 (CO) cm$^{-1}$.

$^1$H NMR (CDCl$_3$) δ 7.41 (m, 3H, Ph), 7.24 (m, 12H, Ph), 6.48 (br, 1H, NH), 3.97 (s, 2H, $CH_2$Cl), 3.12 (q, J=6.3 Hz, 2H, $CH_2$N), 2.43 (t, J=6.3 Hz, 2H, $CH_2$S).

$^{13}$C NMR (CDCl$_3$) δ 165.63 (CO), 144.47, 129.48, 127.97 and 126.81 (Ph), 66.52 (CPh), 42.54 ($CH_2$Cl), 38.35 ($CH_2$N), 31.67 ($CH_2$S).

MS m/z 397 and 395 (M$^+$), 243 ((CPh$_3$)$^+$).

Synthesis of [N-[2-((Triphenylmethyl)thio)ethyl][2-((triphenylmethyl)thio)ethyl-amino]acetamide]

Dissolve N-[2-((Triphenylmethyl)thio)ethyl]-chloroacetamide (5.4 g, 13.8 mmol) and 2-[(triphenylmethyl)thio] ethylamine (4.4 g, 13.8 mmol) in 100 mL dichloromethane, then add triethylamine (3.0 mL, 20.8 mmol) into the solution, heat and reflux for 48 hours. After being cooled, wash with 100 mL sodium bicarbonate aqueous solution (NaHCO$_3$) and take the organic layer. After being dried with anhydrous sodium sulfate and concentrated, liquid chromatography (silicon dioxide, ethyl acetate hexane=1:1) is used for separation and purification so as to get light yellow oil product N-[2-((Triphenylmethyl)thio)ethyl][2-((triphenylmethyl)thio)ethyl-amino]acetamide (2.2 g, 41.8%).

Compound Data of the Product:

IR (neat) v 3330 (NH), 1670 (CO) cm$^{-1}$.

$^1$H NMR (CDCl$_3$) δ 7.42 (m, 4H, HNCO and Ph), 7.20 (m, 30H, Ph), 3.07 (m, 4H, $CH_2$NCO and $CH_2$CO), 2.38 (m, 6H, C$H_2$NHC$H_2$CO and $CH_2$S), 1.94 (br, 1H, NHCH$_2$CO).

$^{13}$C NMR (CDCl$_3$) δ 170.84 (CO), 144.61, 129.47, 127.88 and 126.69 (Ph), 66.72 and 66.65 (CPh$_3$), 51.62 (CH$_2$CO), 48.19 (CH$_2$NHCH$_2$CO), 37.70 (CH$_2$NHCO), 32.12 and 31.97 (CH$_2$S).

MS m/z 243 ((CPH$_3$)$^+$)

Synthesis of Methyl 6-bromohexanoate

Add 6-bromohexanoic acid (4.1 g, 21.1 mmol) into 100 mL absolute methanol solution and then slowly drop 30 mL thionyl chloride into the solution with an ice bath. Stir the solution at room temperature overnight, concentrate the solution and add chloroform to dissolve. After suction filtration, take and concentrate the filtrate to get the product methyl 6-bromohexanoate (4.4 g, 100%).

Compound Data of the Product:

IR (neat) v 11739 (CO) cm$^{-1}$.

$^1$H NMR (CDCl$_3$) δ 3.64 (s, 3H, OCH$_3$), 3.38 (t, 2H, BrCH$_2$), 2.30 (t, 2H, CH$_2$COOCH$_3$), 1.82 (m, 2H, CH$_2$CH$_2$CH$_2$CH$_2$), 1.63 (m, 2H, CH$_2$CH$_2$CH$_2$CH$_2$CH$_2$), 1.46 (m, 2H, CH$_2$CH$_2$CH$_2$CH$_2$CH$_2$).

$^{13}$C NMR (CDCl$_3$) δ 173.77 (CO), 51.73 (COOCH$_3$), 33.72 (BrCH$_2$), 33.34 (CH$_2$CH$_2$CH$_2$CH$_2$CH$_2$), 32.30 (CH$_2$CH$_2$CH$_2$CH$_2$CH$_2$), 27.56 (CH$_2$CH$_2$CH$_2$CH$_2$CH$_2$), 23.98 (CH$_2$CH$_2$CH$_2$CH$_2$CH$_2$).

Synthesis of Methyl 7,10-diaza-9-oxo-7-[2-((triphenylmethyl)thio)-ethyl]-12-[(triphenylmethyl)thio] dodecanoate Take N-[2-((Triphenylmethyl)thio)ethyl][2-((triphenylmethyl)thio)ethyl-amino]acetamide (14.2, 21.0 mmol), add with methyl 6-bromohexanoate (17.6 g, 12.6 mmol), sodium hydroxide (1.76 g, 31.4 mmol), and 100 mL acetonitrile solution, heat and reflux overnight. After being cooled down and suction filtered, take the filtrate and concentrate the filtrate in vacuo. The residue is dissolved in 100 mL dichloromethane, washed with 100 mL water and remove water phase. The organic phase is dehydrated by anhydrous sodium sulfate, concentrated and then purified by liquid chromatography (silicon dioxide, ethyl acetate:hexane=1:1) so as to get Methyl 7,10-diaza-9-oxo-7-[2-((triphenylmethyl)thio)-ethyl]-12-[(triphenylmethyl)thio]dodecanoate (7.4 g, 44%).
Compound Data of the Product:

IR (neat) v 2928 (NH), 1735 and 1674 (CO) cm$^{-1}$.

$^1$H NMR (CDCl$_3$) δ 7.40 (NH), 7.30 (m, 30H, Ph), 3.64 (s, 3H, OCH$_3$), 3.02 (q, 2H, NHC$\underline{H}_2$CH$_2$S), 2.83 (s, 2H, COCH$_2$N), 2.36 (m, 4H, NHCH$_2$C$\underline{H}_2$S and NC$\underline{H}_2$CH$_2$S), 2.24 (m, 6H, NCH$_2$C$\underline{H}_2$S and C$\underline{H}_2$CH$_2$CH$_2$CH$_2$C$\underline{H}_2$), 1.53 (m, 2H, NCH$_2$C$\underline{H}_2$CH$_2$CH$_2$CH$_2$), 1.29 (m, 4H, CH$_2$CH$_2$C$\underline{H}_2$C$\underline{H}_2$CH$_2$).

$^{13}$C NMR (CDCl$_3$) δ 173.90 and 171.13 (CO), 144.68, 144.70, 129.51, 127.86, 126.66, (Ph), 77.43, 77.10 and 76.58 (CPh$_3$), 66.74 (CH$_2$N), 58.23 (CH$_3$O), 54.54 and 53.82 (CH$_2$S), 51.40 (NHCH$_2$), 37.89 (NC$\underline{H}_2$CH$_2$S), 33.89 (C$\underline{H}_2$CH$_2$CH$_2$CH$_2$CH$_2$), 31.97 (CH$_2$CH$_2$CH$_2$CH$_2$C$\underline{H}_2$), 29.94 (CH$_2$C$\underline{H}_2$ CH$_2$CH$_2$CH$_2$), 26.72 (CH$_2$CH$_2$C$\underline{H}_2$CH$_2$CH$_2$), 24.67 (CH$_2$CH$_2$C$\underline{H}_2$CH$_2$CH$_2$).

Synthesis of 7,10-Diaza-9-oxo-7-[2-((triphenylmethyl)thio)-ethyl]-12-[(triphenyl-methyl)thio]dodecanoic acid Dissolve 20 g potassium hydroxide in 200 mL absolute methanol solution, add Methyl 7,10-diaza-9-oxo-7-[2-((triphenylmethyl)thio)-ethyl]-12-[(triphenylmethyl)thio]dodecanoate (7.4 g, 9.2 mmol) into the solution and stir the solution at room temperature overnight. After being concentrated in vacuo at room temperature, add 30 mL water and 30 mL methanol. Adjust pH value of the solution to 7.0 by using concentrated hydrochloric acid. Then extract by 50 mL dichloromethane twice (2×50 mL), remove water phase and take organic phase layer. The organic phase layer is dehydrated by anhydrous sodium sulfate and concentrated in vacuo to get 7,10-Diaza-9-oxo-7-[2-((triphenylmethyl)thio)-ethyl]-12-[(triphenyl-methyl)thio]dodecanoic acid (6.9 g, 94.8%).
Compound Data of the Product:

IR (neat) v 3210 (OH), 2926 (NH), 1679 (CO) cm$^{-1}$.

$^1$H NMR (CD$_3$OD) δ 7.30 (m, 30H, Ph), 3.07 (t, 2H, COCH$_2$N), 2.84 (m, 2H, NHC$\underline{H}_2$CH$_2$S), 2.75 (m, 2H, NCH$_2$S), 2.64 (m, 2H, NC$\underline{H}_2$CH$_2$S), 2.37 (t, 2H, NHCH$_2$C$\underline{H}_2$S), 2.28 (t, 2H, NC$\underline{H}_2$CH$_2$CH$_2$CH$_2$CH$_2$), 1.55 (m, 2H, C$\underline{H}_2$COOH), 1.44 (m, 2H, CH$_2$C$\underline{H}_2$CH$_2$CH$_2$CH$_2$), 1.24 (m, 2H, CH$_2$CH$_2$C$\underline{H}_2$CH$_2$CH$_2$).

$^{13}$C NMR (CD$_3$OD) δ 176.94 and 165.29 (CO), 146.03, 145.45, 130.69, 129.28 and 127.81, 128.99, 128.28, 127.90 (Ph), 68.83 and 67.89 (CPh$_3$), 56 (COCH$_2$), 55.29 (NC$\underline{H}_2$CH$_2$S), 55.13 (NC$\underline{H}_2$CH$_2$CH$_2$CH$_2$CH$_2$), 39.68 (NHC$\underline{H}_2$), 34.44 (NCH$_2$C$\underline{H}_2$S), 32.55 (NHCH$_2$C$\underline{H}_2$S), 26.81 (CH$_2$COOH), 25.29 (CH$_2$C$\underline{H}_2$CH$_2$CH$_2$CH$_2$), 24.52 (CH$_2$CH$_2$C$\underline{H}_2$CH$_2$CH$_2$).

MS m/z 243 ((CPh$_3$)$^+$).

Synthesis of Methty γ-L-Glutamyl-L-glutamate

Add γ-L-Glutamyl-L-glutamic acid (H-Glu(Glu-OH)—OH) (2.0 g, 7.3 mmol) into 50 mL absolute methanol solution and then slowly drop 20 mL thionyl chloride into the solution with an ice bath. Stir the solution at room temperature overnight and concentrate the solution to get the product methyl γ-L-Glutamyl-L-glutamate (2.3 g, 100%).
Compound Data of the Product:

IR (neat) v 3368 (NH$_2$), 2924 (NH), 1735 and 1657 (CO) cm$^{-1}$.

$^1$H NMR (CDCl$_3$) δ 6.9 (br, NH), 4.52 (m, 1H, NH$_2$C$\underline{H}$), 3.67 (s, 3H, OCH$_3$), 3.65 (s, 3H, OCH$_3$), 3.44 (s, 3H$_2$OCH$_3$), 3.40 (q, 1H, NHC$\underline{H}$), 2.32 (q, 2H, CH$_2$C$\underline{H}_2$CONH), 2.00 (m, 4H, C$\underline{H}_2$CH$_2$CONH and C$\underline{H}_2$CH$_2$COOCH$_3$), 1.78 (m, 2H, CH$_2$C$\underline{H}_2$COOCH$_3$).

$^{13}$C NMR (CDCl$_3$) δ175.88, 173.16 and 172.34 (CO), 53.62 (NHCH), 52.35 (NH$_2$CH), 52.07 (CH$_2$C$\underline{H}_2$CONH), 51.71 (CH$_2$C$\underline{H}_2$COO), 51.60 (C$\underline{H}_2$ CH$_2$CONH), 51.50 (C$\underline{H}_2$CH$_2$COO).

MS m/z 320 (M$^+$-Cl).

Synthesis of Trimethyl-γ-L-glutamyl-L-glutamyl-7,10-Diaza-9-oxo-7-[2-(triphenylmethyl)thioethyl]-12-[(triphenylmethyl)-thio]dodecanamide Take 7,10-diaza-9-oxo-7-[2-((triphenylmethyl)thio)-ethyl]-12-[(triphenyl-methyl)thio]dodecanoic acid (0.55 g, 0.69 mmol), add with methyl γ-L-Glutamyl-L-glutamate (0.22 g, 0.69 mmol), triethylamine (0.24 mL, 1.7 mmol), N-hydroxysuccinimide (0.10 g, 0.83 mmol), 1,3-dicyclohexylcarbodiimide (0.2 g, 0.1 mmol), and 50 mL chloroform. Stir the solution at room temperature for 48 hours, suction filter, take the filtrate and wash the filtrate with water. The residue is dissolved in 100 mL acetone, then filter by suction and take the filtrate. The organic phase is dehydrated by anhydrous sodium sulfate, concentrated and purified by liquid chromatography (silicon dioxide, chloroform:methanol=95:5) so as to get Trimethyl-γ-L-glutamyl-L-glutamyl-7,10-Diaza-9-oxo-7-[2-(triphenylmethyl)thioethyl]-12-[(triphenylmethyl)-thio]dodecanamide (0.31 g, 42.4%).
Compound Data of the Product:

IR (neat) v 3308 and 2927 (NH), 1741 and 1659 (CO) cm$^{-1}$.

$^1$H NMR (CDCl$_3$) δ7.46 (br, 1H, N$\underline{H}$CH$_2$CH$_2$S), 7.25 (m, 30H, Ph), δ 6.80 (br, 1H, CH$_2$CH$_2$CH$_2$CH$_2$CH$_2$CON$\underline{H}$), 6.50 (br, 1H, CH$_2$CH$_2$CON$\underline{H}$), 4.57 (m, 2H, NHC$\underline{H}$COOH$_3$), 3.72 (s, 6H, OCH$_3$), 3.66 (s, 3H, OCH$_3$), 3.00 (q, 2H, NHC$\underline{H}_2$CH$_2$S), 2.83 (s, 2H, COCH$_2$N), 2.19 (m, 16H, NHCH$_2$C$\underline{H}_2$S, NC$\underline{H}_2$CH$_2$S, NC$\underline{H}_2$CH$_2$CH$_2$CH$_2$C$\underline{H}_2$ and C$\underline{H}_2$CH$_2$CO), 1.56 (m, 2H, NCH$_2$C$\underline{H}_2$CH$_2$CH$_2$CH$_2$), 1.23 (m, 4H, NCH$_2$CH$_2$C$\underline{H}_2$C$\underline{H}_2$CH$_2$).

$^{13}$C NMR (CDCl$_3$) δ 173.19, 173.14, 172.39, 172.14, 172.07 and 171.28 (CO), 144.71, 144.67, 129.51, 127.87 and 126.67 (Ph), 77.45, 77.03 and 76.60 (CPh$_3$), 66.47 (COC$\underline{H}_2$), 58.13 and 54.56 (NHC$\underline{H}$), 53.81 (CH$_2$C$\underline{H}_2$CONH), 52.45 (C$\underline{H}_2$CH$_2$CO), 51.76 (CH$_2$C$\underline{H}_2$CO), 37.90 (NC$\underline{H}_2$CH$_2$), 36.06 (NHC$\underline{H}_2$CH$_2$), 32.18 (NHCH$_2$C$\underline{H}_2$) 31.95 (NCH$_2$C$\underline{H}_2$S), 30.02 (NCH$_2$C$\underline{H}_2$CH$_2$CH$_2$CH$_2$), 27.90 (NCH$_2$C$\underline{H}_2$CH$_2$CH$_2$CH$_2$), 27.09, 26.80 and 26.61 (OCH$_3$), 251.15 (NCH$_2$CH$_2$CH$_2$CH$_2$C$\underline{H}_2$).

MS m/z 243 ((CPh$_3$)$^+$).

Synthesis of 7,10-Diaza-9-oxo-7-[2-(triphenylmethyl)-thioethyl]-12-[(triphenylmethyl)thio]-dodecanamide-γ-L-glutamyl-L-glutamic acid (DODGA)

Dissolve 2 g potassium hydroxide in 20 mL absolute methanol solution, add trimethyl-γ-L-glutamyl-L-glutamyl-7,10-Diaza-9-oxo-7-[2-(triphenylmethyl)thioethyl]-12-[(triphenylmethyl)-thio]dodecanamide (0.15 g, 0.15 mmol) into the solution and stir the solution at room temperature for 30 min. Add 10 mL water into the solution and adjust pH value of the solution into 7.0 by using concentrated hydrochloric acid. Then extract by 20 mL dichloromethane twice (2×20 mL), remove water phase and take organic phase layer.

The organic phase layer is dehydrated by anhydrous sodium sulfate and concentrated in under reduced pressure to get DODGA (0.15 g, 100%).

Compound Data of the Product:

IR (neat) v 3310 (OH), 3008 and 2927 (NH), 1741 and 1659 (CO) $cm^{-1}$.

$^1$H NMR (CD$_3$OD) δ 7.22 (m, 30H, Ph), 4.42 (m, 2H, NHC$\underline{H}$), 3.65 (s, 2H, COC$\underline{H}_2$), 3.05 (t, 2H, NHC$\underline{H}_2$CH$_2$S), 2.86 (m, 2H, C$\underline{H}_2$CH$_2$CH$_2$CH$_2$CH$_2$), 2.77 (m, 2H, NC$\underline{H}_2$CH$_2$S), 2.65 (m, 2H, NCH$_2$C$\underline{H}_2$S), 2.35 (m, 4H, NHCH$_2$C$\underline{H}_2$S and CH$_2$C$\underline{H}_2$CO), 2.22 (m, 6H, C$\underline{H}_2$CH$_2$CONH, C$\underline{H}_2$CH$_2$COOH and CH$_2$CH$_2$CH$_2$CH$_2$C$\underline{H}_2$), 1.99 (m, 2H, CH$_2$C$\underline{H}_2$COOH), 1.58 (m, 2H, CH$_2$C$\underline{H}_2$CH$_2$CH$_2$CH$_2$), 1.45 (m, 2CH$_2$CH$_2$CH$_2$C$\underline{H}_2$CH$_2$), 1.27 (m, 2H, CH$_2$CH$_2$C$\underline{H}_2$CH$_2$CH$_2$).

$^1$H NMR (CD$_3$OD) δ 175.14, 174.72, 174.58, 173.83, 173.79 and 173.76 (CO), 144.91, 144.33, 129.58, 128.19, 127.91, 127.18 and 126.81 (Ph), 78.38 (CPh$_3$), 67.71 (CH), 66.77, (COC$\underline{H}_2$), 54.03 (NHC$\underline{H}_2$CH$_2$S), 51.85 (C$\underline{H}_2$CH$_2$CH$_2$CH$_2$CH$_2$), 38.59 (NC$\underline{H}_2$CH$_2$S), 34.99 (NCH$_2$C$\underline{H}_2$S), 31.42 (NHCH$_2$CH$_2$S), 30.18 (C$\underline{H}_2$CH$_2$CO), 26.63 (CH$_2$C$\underline{H}_2$CO), 25.59 (CH$_2$C$\underline{H}_2$CH$_2$CH$_2$CH$_2$), 24.81 (CH$_2$ CH$_2$C$\underline{H}_2$CH$_2$), 23.30 (CH$_2$CH$_2$C$\underline{H}_2$CH$_2$CH$_2$).

MS m/z 243 ((CPh$_3$)$^+$).

Synthesis of 6'-(N-Benzyloxycarbonyl)aminohexanol

Dissolve 6'-aminohexanol (5.9 g, 50.0 mmol) in 20 mL water, add with sodium carbonate (3.2 g, 30.0 mmol) and set the solution in an ice bath. Dissolve benzyl chlorocarbonate (7.3 g, 50.0 mmol) in 20 mL diethyl ether and slowly drop this solution into the above solution. Then stir the mixture at room temperature for 2 hours. Filter the mixture and wash solid with a little amount of diethyl ether. Remove the solvent from the solid in a vacuum system to get 6'-(N-Benzyloxycarbonyl) aminohexanol (9.2 g, 73.2%).

Compound Data of the Product:

IR (neat) v 3382 and 1530 (NH), 3336 (OH), 1688 (CO) $cm^{-1}$.

$^1$H NMR (CDCl$_3$) δ 7.34 (m, 5H, Ph), 5.08 (s, 2H, PhC$\underline{H}_2$), 4.90 (br, 1H, NH), 3.60 (t, J=6.5 Hz, 2H, C$\underline{H}_2$OH), 3.17 (q, J=6.6 Hz, 2H, NHC$\underline{H}_2$), 1.93 (br, 1H, OH), 1.52 (m, 4H, C$\underline{H}_2$CH$_2$CH$_2$C$\underline{H}_2$CH$_2$O), 1.35 (m, 4H, C$\underline{H}_2$C$\underline{H}_2$CH$_2$CH$_2$O).

$^{13}$C NMR (CDCl$_3$) δ 156.45 (CO), 136.55, 128.42 and 127.99 (Ph), 66.51 (CH$_2$OH), 62.52 (PhCH$_2$), 40.82 (NHCH$_2$), 32.45 (C$\underline{H}_2$CH$_2$OH), 29.84 (NHCH$_2$C$\underline{H}_2$), 26.28 (C$\underline{H}_2$CH$_2$CH$_2$OH), 25.22 (C$\underline{H}_2$CH$_2$CH$_2$CH$_2$OH). MS m/z 251 (M$^+$).

Synthesis of 2-Acetamido-2,4,6,-tri-O-acetyl-1-chloro-1,2-dideoxy-α-D-galactopyranose Cool down 30 mL acetyl chloride to 0° C., add with N-acetyl-D-galactosamine (3.0 g, 13.6 mmol), seal the solution with a cover, then set and stir the solution in a thermostatic chamber at 10° C. After 5 days, add 80 mL dichloromethane into the solution and mix evenly. Then add 160 mL ice water into the solution, mix evenly and wait until the two phases separate. The organic phase is washed once by 50 mL saturated sodium bicarbonate aqueous solution (1×50 mL) and then is dehydrated anhydrous sodium sulfate. After evaporation of the solvenet under reduced pressure, sticky oil product 2-Acetamido-2,4,6,-tri-O-acetyl-1-chloro-1,2-dideoxy-α-D-galactopyranose (2.45 g, 51%) is obtained.

Compound Data of the Product:

IR (neat) v 3289 and 1544 (NH), 1750 and 1666 (CO) $cm^{-1}$.

$^1$H NMR (CDCl$_3$) δ 6.28 (d, J=3.6 HZ, 1H, H$_1$), 5.94 (d, J=8.7 Hz, 1H, NH), 5.46 (dd, J=3.2 and 1.4 Hz, 1H, H$_4$), 5.29 (dd, J=11.4 and 3.3 Hz, 1H, H$_3$), 4.79 (m, 1H, H$_2$), 4.48 (t, J=6.9 Hz, 1H, H$_5$), 4.19 (m, 2H, H$_6$), 2.17 (s, 3H, CH$_3$), 2.10 (s, 3H, CH$_3$), 2.03 (s, 3H, CH$_3$), 2.01 (s, 3H, CH$_3$).

$^{13}$C NMR (CDCl$_3$) δ 170.65, 170.48, 170.26 and 169.95 (CO), 94.97 (C$_1$), 69.73 (C$_5$), 67.27 (C$_4$), 66.48 (C$_3$), 61.06 (C$_2$), 49.12 (C$_6$), 22.91, 20.56, 20.52 and 20.49 (CH$_3$).

MS m/z 330 (M$^+$-Cl)

Synthesis of 6'-(N-Benzyloxycarbonyl)aminohexyl-2-acetamido-3,4,6-tri-O-acetyl-2-deoxy-β-D-galactopyranoside Dissolve 6'-(N-Benzyloxycarbonyl)aminohexanol (0.72 g, 2.86 mmol), 2-Acetamido-2,4,6,-tri-O-acetyl-1-chloro-1,2-dideoxy-α-D-galactopyranose (1.05 g, 2.86 mmol), anhydrous calcium sulfate (0.3 g) and mercuric cyanide (0.88 g, 3.5 mmol) in a mixture of 15 mL toluene and 15 mL nitromethane. Stir the mixture solution at room temperature for 24 hours and then filter the mixture solution. The filtrate is concentrated in vacuo, then dissolve residue in 80 mL dichloromethane and wash with 50 mL water twice (2×50 mL). The organic phase is dried by anhydrous sodium sulfate, concentrated under reduced pressure, separated and purified by liquid chromatography (silicon dioxide, chloroform methanol=95:5). Thus colorless solid product 6'-(N-Benzyloxycarbonyl)aminohexyl 2-acetamido-3,4,6-tri-O-acetyl-2-deoxy-β-D-galactopyranoside (0.58 g, 35%) is obtained.

Compound Data of the Product:

IR (KBr) v 3318 and 1543 (NH), 1748 and 1668 (CO) $cm^{-1}$.

$^1$H NMR (CDCl$_3$) δ 7.35 (m, 5H, Ph), 5.94 (d, J=8.4 Hz, NH), 5.33 (d, J=3.0 H2, H$_4$), 5.26 (dd, J=11.3 and 3.2 Hz, 1H, H$_3$), 5.11 (AB, J=12.3 Hz, 2H, CH$_2$Ph), 4.90 (br, 1H, NH), 4.65 (d, J=8.4 Hz, 1H, H$_1$), 4.12 (m, 2H, H$_6$), 4.02-3.81 (m, 3H, H$_2$, H$_5$, and OC$\underline{H}_2$CH$_2$), 3.48 (m, 1H, OC$\underline{H}_2$CH$_2$), 3.21 (m, 2H, CH$_2$N), 2.13 (s, 3H, CH$_3$), 2.05 (s, 3H, CH$_3$), 2.0 (s, 3H, CH$_3$), 1.94 (s 3H, CH$_3$), 1.51 (m, 4H, OCH$_2$C$\underline{H}_2$CH$_2$CH$_2$C$\underline{H}_2$CH$_2$), 1.34 (m, 4H, OCH$_2$CH$_2$C$\underline{H}_2$C$\underline{H}_2$).

$^{13}$C NMR (CDCl$_3$) δ 170.44 and 156.56 (CO), 136.64, 128.49, 128.04 and 127.84 (Ph), 100.73 (C$_1$), 70.51, (C$_5$), 69.36 (C$_4$), 69.34 (C$_3$), 66.79 (CH$_2$Ph), 66.53 (OC$\underline{H}_2$CH$_2$), 61.44 (C$_6$), 51.54 (C$_2$), 40.55 (CH$_2$NH), 29.70 (OCH$_2$C$\underline{H}_2$), 28.93 (NHCH$_2$C$\underline{H}_2$), 25.89 (OCH$_2$CH$_2$C$\underline{H}_2$), 25.07 (C$\underline{H}_2$CH$_2$CH$_2$N), 23.35 (C$\underline{H}_3$CONH), 20.67 (C$\underline{H}_3$COO).

$^1$H NMR (CD$_3$OD) δ 7.34 (m, 5H, Ph), 5.32 (d, J=3.3 Hz, 1H, H$_4$), 5.05 (m, 3H, H$_3$ and CH$_2$Ph), 4.54 (d, J=8.4 Hz, 1H, H$_1$), 4.15-3.95 (m, 4H, H$_2$, H$_5$ and H$_6$), 3.83 (m, 1H, OCH$_2$), 3.48 (m, 1H, OCH$_2$), 3.10 (t, J=6.9 Hz, 2H, CH$_2$N), 2.13 (s 3H, CH$_3$), 2.01 (s, 3H, CH$_3$), 1.94 (s, 3H, CH$_3$), 1.91 (s, 3H, CH$_3$), 1.51 (m, 4H, OCH$_2$C$\underline{H}_2$CH$_2$CH$_2$C$\underline{H}_2$), 1.34 (m, 4H, OCH$_2$CH$_2$C$\underline{H}_2$CH$_2$).

$^{13}$C NMR (CD$_3$OD) δ 173.52, 172.13 and 171.11 (CO), 158.88, 138.55, 129.49 and 128.96 and 128.74 (Ph), 102.66 (C$_1$), 72.17 (C$_5$), 71.76 (C$_4$), 70.70 (C$_3$), 68.25 (CH$_2$Ph), 67.27 (OC$\underline{H}_2$CH$_2$), 62.79 (C$_6$), 51.69 (C$_2$), 41.73 (CH$_2$N), 30.89 (OCH$_2$C$\underline{H}_2$), 30.51 (NHCH$_2$C$\underline{H}_2$), 27.45 (OCH$_2$CH$_2$C$\underline{H}_2$), 26.68 (C$\underline{H}_2$CH$_2$CH$_2$N), 22.93 (CH$_3$), 20.65 (CH$_3$).

MS m/z 521 (M$^+$-CH$_3$).

Synthesis of 6'-Aminohexyl 2-acetamio-3,4,6-tri-O-acetyl-2-deoxy-β-D-galactopyranoside (ah-Gal-NAc$_4$)

Dissolve 6'-(N-Benzyloxycarbonyl)aminohexyl 2-acetamido-3,4,6-tri-O-acetyl-2-deoxy-β-D-galactopyranoside (0.66 g, 1.14 mmol) in 20 mL alcohol and add 10% palladium carbon catalyst (0.08 g) into the solution. Set the solution in a reduction device and vibrate the solution in 50 psi hydrogen gas. After 15-24 hours, filter the solution and dry the filtrate under reduced pressure to get ah-GalNAc$_4$ (0.51 g, 100%).
Compound Data of the Product:
IR (neat) v 3256 and 3377 ($NH_2$), 1747 and 1657 (CO) $cm^{-1}$.
$^1$H NMR ($CD_3OD$) δ 5.33 (d, J=2.7 Hz, 1H, $H_4$), 5.05 (dd, J=11.4 and 3.3 Hz, 1H, $H_3$), 4.55 (d, J=8.4 Hz, 0.1H, $H_1$), 4.18-3.97 (m, 4H, $H_2$, $H_5$ and $H_6$), 3.86 (m, 1H, O$CH_2$), 3.52 (m, 1H, O$CH_2$), 2.92 (t, J=7.5 Hz, 2H, $CH_2$N), 2.14 (s, 3H, $CH_3$), 2.02 (s, 3H, $CH_3$), 1.94 (s, 3H, $CH_3$), 1.93 (s, 3H, $CH_3$), 1.46 (m, 4H, O$CH_2CH_2CH_2CH_2CH_2$), 1.42 (m, 4H, O$CH_2CH_2CH_2CH_2$).
$^{13}$C NMR ($CD_3OD$) δ 172.03, 171.97 and 171.61 (CO), 102.66 ($C_1$), 72.12 ($C_5$), 71.76 ($C_4$), 70.64 ($C_3$), 68.17 (O$CH_2$), 67.72 ($C_6$), 51.52 ($C_2$), 40.75 ($CH_2$N), 30.19 (O$CH_2CH_2$), 28.36 ($CH_2CH_2$N), 27.02 (O$CH_2CH_2CH_2$), 26.35 ($CH_2CH_2CH_2$N), 22.95 ($CH_3$), 20.58 ($CH_3$).
MS m/z 446 ($M^+$), 387 ($M^+$-$CH_3COO$).

Synthesis of 6-Tri-o-(2'-acetamido-3',4',6'-tri-o-acetyl-2'-deoxy-(3-D-galactopyranoside) hexyl 7,10-diaza-9-oxo-7-[2-(triphenylmethyl)thioethyl]-12-[(triphenylmethyl)thio]-dodecanamido-γ-L-glutamyl-L-glutamate Take and put DODGA (1.32 g, 1.31 mmol), ah-GalNAc$_4$ (1.21 g, 5.87 mmol), triethylamine (0.82 mL, 5.87 mmol), 1,3-dicyclohexylcarbodiimide (1.21 g, 5.87 mmol), N-hydroxysuccinimide (0.68 g, 5.87 mmol), and 80 mL chloroform into a 250 mL round-bottom flask, heat to 65° C. and reflux for 24 hours. Concentrate the solution, dissolve EA in solution, concentrate the solution again and use liquid chromatography (silicon dioxide, chloroform methanol=95:5) for separation and purification so as to get a product 6-Tri-o-(2'-acetamido-3',4',6'-tri-o-acetyl-2'-deoxy-β-D-galactopyranoside) hexyl 7,10-diaza-9-oxo-7-[2-(triphenylmethyl)thioethyl]-12-[(triphenylmethyl)thio]-dodecanamido-γ-L-glutamyl-L-glutamate (1.12 g, 37%).
Compound Data of the Product:
IR (neat) v 3287 and 2929 and 1538 (NH), 1748 and 1658 (CO) $cm^{-1}$.
$^1$H NMR ($CDCl_3$) δ7.42 (NH), 7.40-7.15 (m, 12H, Ph), 6.8-6.4 (NH), 5.35 (s, C$H$OAC), 5.30 (m, NHC$H$CO), 5.15 (m, OC$H$O), 4.67 (t, C$H_2$OAC), 4.14 (m, C$H$NHAC), 3.91 (m, C$H$C$H_2$OAC), 3.70 (m, $CH_2CH_2$O), 3.45 (m, C$H_2CH_2$O), 3.20 (m, NHC$H_2CH_2$S), 3.00 (q, NC$H_2CH_2$S), 2.83 (s, COC$H_2$N), 2.37 (m, NHC$H_2CH_2$S and NC$H_2CH_2$S), 2.22 (C$H_2CH_2$CO), 2.05 (m, OAC), 1.54 (m, C$H_2$C$H_2CH_2CH_2CH_2$), 1.34 (m, $CH_2CH_2CH_2CH_2CH_2CH_2$).
MS m/z 2335 ($M^+$), 2357 ($M^+Na$)$^+$ Synthesis of 6-Tri-o-(2'-acetamido-3',4',6'-trihydroxy-2'-deoxy-β-D-galactopyranoside) hexyl 7,10-diaza-9-oxo-7-[2-(triphenylmethyl)-thioethyl]-12-[(triphenylmethyl)thio)-dodecanamido-γ-L-glutamyl-L-glutamate]

Dissolve 6-Tri-o-(2'-acetamido-3',4',6'-tri-o-acetyl-2'-deoxy-β-D-galactopyranoside) hexyl 7,10-diaza-9-oxo-7-[2-(triphenylmethyl)thioethyl]-12-[(triphenylmethyl)thio]-dodecanamido-γ-L-glutamyl-L-glutamate (1.12 g, 0.48 mmol) in 20 mL absolute methanol solution. Then add sodium methylate/methanol solution (0.5M, 0.93 mL) into the solution and stir the mixture at room temperature for 15 min. Slowly drop 0.1N hydrochloric acid solution into the mixture with an ice bath and adjust pH value of the mixture into 6. After being concentrated under reduced pressure, (ah-GalNAc)$_3$-DODGA (0.94 g, 100%) is obtained.
Compound Data of the Product:
IR (KBr) v 3400 (OH), 2930 and 1539 (NH), 1630 (CO) $cm^{-1}$.
$^1$H NMR ($CD_3OD$) δ7.32-7.17 (m, 12H, Ph), 7.46 (d, CHOH), 4.20 (m, C$H$CO), 3.95 (m, CHCHOH), 3.81 (m, OCHO), 3.77 (m, COC$H_2$), 3.68 (d, C$H_2$OH), 3.53 (m, $CH_2$C$H_2$O), 3.41 (m, C$H_2CH_2$O), 3.23 (m, NHC$H_2CH_2$S), 2.95 (m, NC$H_2CH_2$S), 2.60 (t, NHC$H_2CH_2$), 2.29 (m, $CH_2CH_2$CO), 2.10 (m, C$H_2CH_2$CO), 1.90 (s, NHAc), 1.45 (m, C$H_2$C$H_2CH_2CH_2CH_2CH_2$), 1.26 (m, $CH_2CH_2CH_2CH_2CH_2CH_2$).
MS m/z 1957 ($M^+$), 1981 ($M^+Na$)$^+$.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A precursor used for labeling hepatocyte receptor and containing trisaccharide and a diamide dimercaptide ($N_2S_2$) ligand is represented by the following structural formula

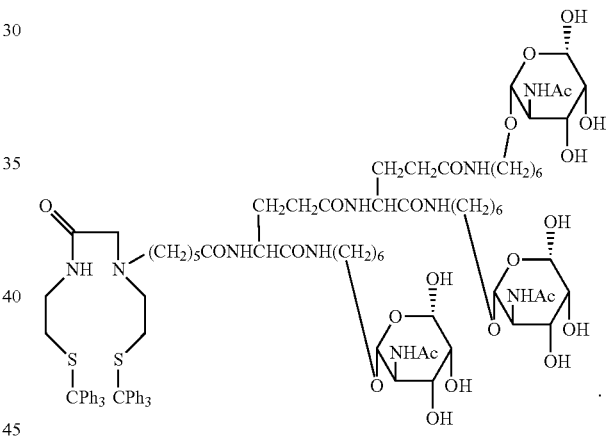

2. A method for preparing a precursor used for labeling hepatocyte receptor and containing trisaccharide and a diamide dimercaptide ($N_2S_2$) ligand comprising the steps of:
synthesizing a carboxylic acid of a bifunctional chelating agent containing a diamide dimercaptide ($N_2S_2$) ligand;
amidating the carboxylic acid to form an amide of the bifunctional chelating agent containing $N_2S_2$ ligand and further hydrolyzing the amide to get three polycarboxyl groups;
synthesizing three galactosides; and
using the galactosides to amidate the polycarboxyl groups of the amide and get a precursor used for labeling hepatocyte receptors and containing trisaccharide and a $N_2S_2$ ligand.

3. The method as claimed in claim 2, wherein the carboxylic acid is 7,10-diaza-9-oxo-7-[2-((triphenylmethyl)thio)-ethyl]-12-[(triphenyl-methyl)thio]dodecanoic acid.

4. The method as claimed in claim 3, wherein the step of synthesizing a carboxylic acid further includes the steps of:
step (1) taking 2-thioethylamine hydrochloride and triphenylmethanol to react under catalysis of boron trifluoride-diethyl ether complex for protecting thiol groups and get 2-[(triphenylmethyl)thio]ethylamine;

step (2) using 2-[(Triphenylmethyl)thio]ethylamine and chloroacetyl chloride to carry out the amidation reaction in trichloromethane solution so as to produce N-[2-((Triphenylmethyl)thio)ethyl]-chloroacetamide;

step (3) taking 2-[(Triphenylmethyl)thio]ethylamine, and N-[2-((Triphenylmethyl)thio)ethyl]-chloroacetamide and using triethylamine used as a reagent to carry out the substitution reaction in dichloromethane solution and get an amine-amide-thiol ligand;

step (4) dissolving 6-bromohexanoic acid and thionyl chloride in absolute methanol solution to carry out the esterification reaction and get methyl 6-bromohexanoate;

step (5) taking the amine-amide-thiol ligand and methyl 6-bromohexanoate and using sodium hydroxide (NaOH) as a reagent to carry out the substitution reaction in acetonitrile solution and get methyl 7,10-diaza-9-oxo-7-[2-((triphenylmethyl)thio)-ethyl]-12-[(triphenylmethyl)thio]dodecanoate;

step (6) hydrolyzing methyl 7,10-diaza-9-oxo-7-[2-((triphenylmethyl)thio)-ethyl]-12-[(triphenylmethyl)thio]dodecanoate in alkaline methanol solution to get 7,10-diaza-9-oxo-7-[2-((triphenylmethyl)thio)-ethyl]-12-[(triphenyl-methyl)thio]dodecanoic acid.

5. The method as claimed in claim 2, wherein the carboxylic acid of the bifunctional chelating agent containing the diamide dimercaptide ($N_2S_2$) ligand uses a trityl group as a protecting group.

6. The method as claimed in claim 4, wherein in the step (1), reaction temperature of the reaction for protecting thiol groups is 72 degrees Celsius and reaction time is 4 hours.

7. The method as claimed in claim 4, wherein in the step (3), reaction temperature of the substitution reaction is 55° C. and reaction time is 48 hours.

8. The method as claimed in claim 4, wherein in the step (4), reaction temperature of the esterification reaction is 25° C. and the reaction time is 24 hours.

9. The method as claimed in claim 4, wherein in the step (5), reaction temperature of the substitution reaction is 85° C. and the reaction time is 24 hours.

10. The method as claimed in claim 2, wherein the amide is trimethyl-γ-L-glutamyl-L-glutamyl-7,10-Diaza-9-oxo-7-[2-(triphenylmethyl)thioethyl]-12-[(triphenylmethyl)-thio]dodecanamide.

11. The method as claimed in claim 10, wherein the step of amidating the carboxylic acid further includes the steps of:

step (7) dissolving γ-L-glutamyl-L-glutamic acid and thionyl chloride in absolute methanol solution to carry out the esterification reaction and get methyl γ-L-glutamyl-L-glutamate, step (8) taking methyl γ-L-glutamyl-L-glutamate and the carboxylic acid and using 1,3-dicyclohexylcarbodiimide as well as N-hydroxysuccinimide as a reagent to carry out the amidation reaction in chloroform solution and get trimethyl-γ-L-glutamyl-L-glutamyl-7,10-diaza-9-oxo-7-[2-(triphenylmethyl)thioethyl]-12-[(triphenylmethyl)-thio]dodecanamide.

12. The method as claimed in claim 11, wherein in the step (7), reaction temperature of the esterification reaction is 25 degrees Celsius and reaction time is 24 hours.

13. The method as claimed in claim 11, wherein in the step (8), reaction temperature of the amidation reaction is 25 degrees Celsius and reaction time is 48 hours.

14. The method as claimed in claim 10, wherein the amide is hydrolyzed to form a compound DODGA whose structural formula is:

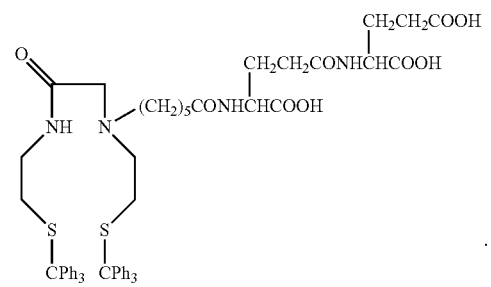

15. The method as claimed in claim 2, wherein the galactoside is 6'-aminohexyl-2-acetamido-3,4,6-tri-O-acetyl-2-deoxy-β-D-galactoside, ah-GalNAc$_4$, having a structural formula of:

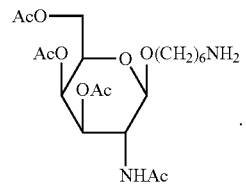

16. The method as claimed in claim 15, wherein the step of synthesizing the galatosides further includes steps of step (9) using 6'-aminohexanol and benzyl chlorocarbonate to carry out an amino protecting reaction and get a 6'-(N-Benzyloxycarbonyl)aminohexanol;

step (10) taking N-acetyl-D-galactosamine and acetyl chloride to react at 10° C. and get 2-Acetamido-2,4,6,-tri-O-acetyl-1-chloro-1,2-dideoxy-α-D-galactopyranose;

step (11) using 6'-(N-Benzyloxycarbonyl)aminohexanol and 2-Acetamido-2,4,6,-tri-O-acetyl-1-chloro-1,2-dideoxy-α-D-galactopyranose to perform substitution reaction in a mixture solution of toluene and nitromethane with a catalyst of mercuric cyanide and get 6'-(N-Benzyloxycarbonyl)aminohexyl-2-acetamido-3,4,6-tri-O-acetyl-2-deoxy-β-D-galactopyranoside;

step (12) hydrogenizing/reducing 6'-(N-Benzyl oxycarbonyl)aminohexyl-2-acetamido-3,4,6-tri-O-acetyl-2-deoxy-β-D-galactopyranoside in alcohol and in the presence of a palladium carbon catalyst to get the 6'-aminohexyl-2-acetamido-3,4,6-tri-O-acetyl-2-deoxy-β-D-galactoside.

17. The method as claimed in claim 2, wherein in the step of using the galactosides to amidate the polycarboxyl groups of the amide, the amide is hydrolyzed to form a compound DODGA and the galactoside is 6'-aminohexyl-2-acetamido-3,4,6-tri-O-acetyl-2-deoxy-β-D-galactoside, ah-GalNAc$_4$; the step of using the galactosides to amidate the polycarboxyl groups of the amide further includes the steps of:

step (13) activating a carboxylic acid of DODGA to react with ah-GalNAc$_4$ and using 1,3-dicyclohexylcarbodiimide as well as N-hydroxysuccinimide as a reagent to carry out the amidation reaction in chloroform solution and get 6-Tri-o-(2'-acetamido-3',4',6'-tri-o-acetyl-2'-deoxy-β-D-galactopyranoside) hexyl 7,10-diaza-9-oxo-7-[2-(triphenylmethyl)thioethyl]-12-[(triphenylmethyl)thio]-dodecanamido-γ-L-glutamyl-L-glutamate; and step (14) hydrolyzing 6-Tri-o-(2'-acetamido-3',4',6'-tri-o-acetyl-2'-deoxy-β-D-galactopyranoside)hexyl 7,10-diaza-9-oxo-7-[2-(triphenylmethyl)thioethyl]-12-[(triphenylmethyl)thio]-dodecanamido-γ-L-glutamyl-L-glutamate with sodium methylate to get 6-Tri-o-(2'-acetamido-3',4',6'-trihydroxy-2'-deoxy-β-D-galactopyranoside)hexyl 7,10-diaza-9-oxo-7-[2-(triphenylmethyl)thioethyl]-12-[(triphenylmethyl)thio]-dodecanamido-γ-L-glutamyl-L-glutamate, which is (ah-GalNAc)$_3$-DODGA.

18. A radiotracer of a precursor used for labeling hepatocyte receptor and containing trisaccharide and a diamide dimercaptide (N$_2$S$_2$) ligand is represented by the following structural formula:

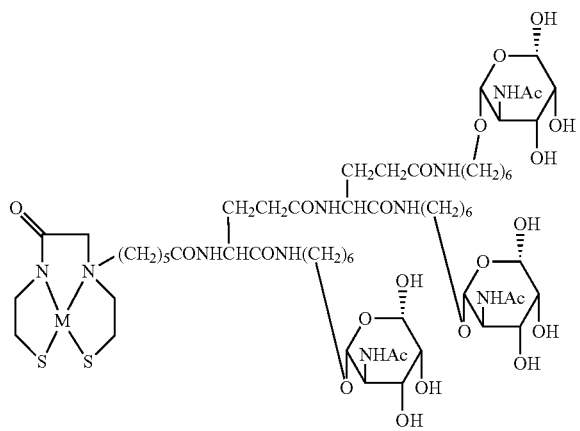

wherein M is selected from the group consisting of $^{99m}$Tc, $^{188}$Re and $^{111}$In.

19. A pharmaceutical composition of a precursor used for labeling hepatocyte receptor and containing trisaccharide and a diamide dimercaptide (N$_2$S$_2$) ligand is used to treat liver cancers and is represented by the following structural formula:

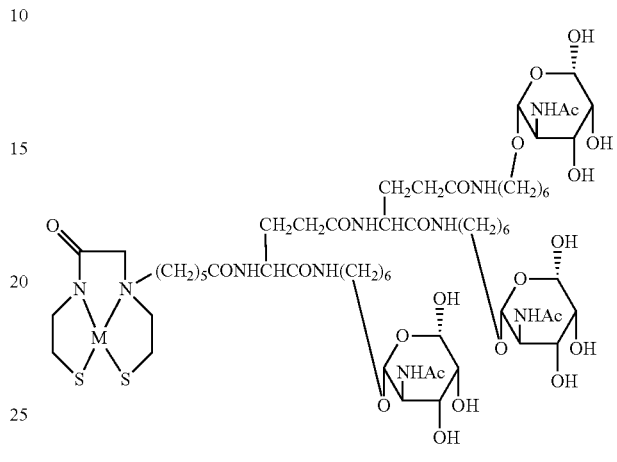

wherein M is selected from the group consisting of $^{99m}$Tc, $^{188}$Re and $^{111}$In.

* * * * *